US00PP16230P3

(12) United States Plant Patent

Bellenot-Kapusta et al.

(10) Patent No.: US PP16,230 P3
(45) Date of Patent: Jan. 31, 2006

(54) *COTONEASTER* PLANT NAMED 'BELKA'

(50) Latin Name: *Cotoneaster dammeri*
Varietal Denomination: Belka

(75) Inventors: Véronique Bellenot-Kapusta, Beaucouzé (FR); Alain Cadic, Beaucouzé (FR)

(73) Assignee: Agri-Obtentions S.A., Guyancourt (FR)

( * ) Notice: Subject to any disclaimer, the term of this patent is extended or adjusted under 35 U.S.C. 154(b) by 96 days.

(21) Appl. No.: 10/912,158

(22) Filed: Aug. 6, 2004

(65) Prior Publication Data

US 2005/0044601 P1 Feb. 24, 2005

(30) Foreign Application Priority Data

Aug. 20, 2003 (FR) ..... 18551

(51) Int. Cl.
*A01H 5/00* (2006.01)

(52) U.S. Cl. ..... Plt./226

(58) Field of Classification Search ..... Plt./226
See application file for complete search history.

*Primary Examiner*—Anne Marie Grunberg
*Assistant Examiner*—June Hwu
(74) *Attorney, Agent, or Firm*—Burns, Doane, Swecker & Mathis, LLP

(57) ABSTRACT

A new and distinct *Cotoneaster dammeri* cultivar is provided which unlike previously known cultivars displays very good tolerance to fire blight (*Erwinia amylovora*). The foliage is attractive dense medium green and is semi-glossy on the upper surface and dull and pubescent on the under surface. A creeping growth habit with erect branching is displayed. Good cold tolerance has been observed. The new cultivar is well suited for use as an improved attractive low-growing ornamental ground cover.

5 Drawing Sheets

Figure 1:
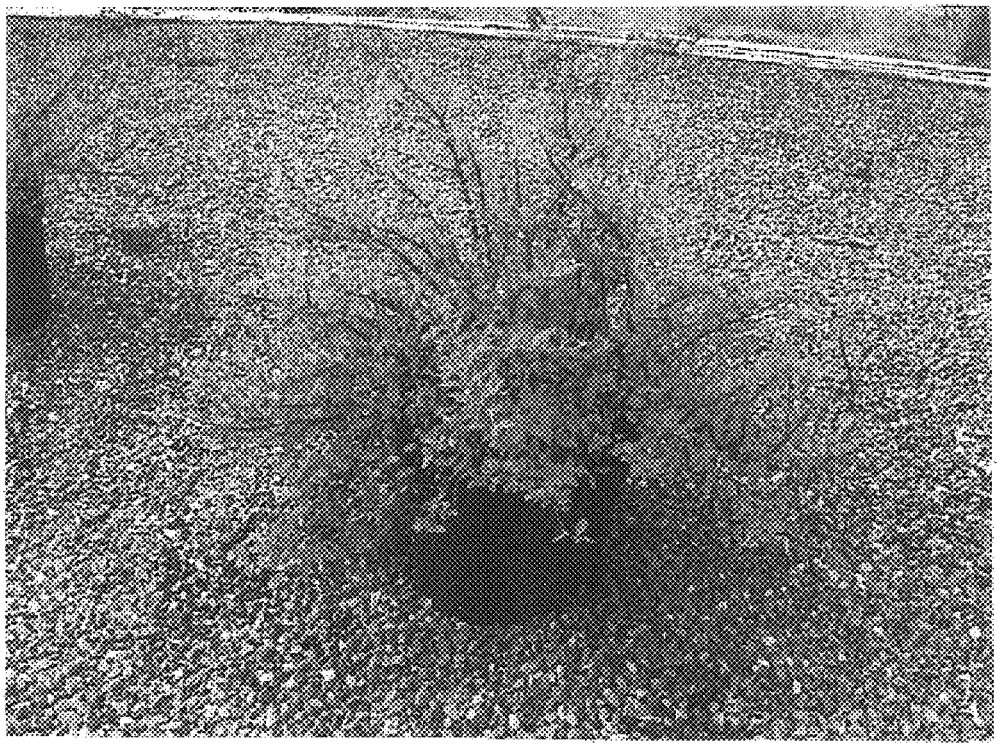

Botanical/commercial classification: *Cotoneaster dammeri/Cotoneaster* Plant.
Varietal denomination: cv. 'Belka'.

SUMMARY OF THE INVENTION

The present invention relates to a new and distinct *Cotoneaster* cultivar of the evergreen type that is botanically known as *Cotoneaster dammeri.*

The new cultivar is the result of the open pollination of the 'Eichholz' cultivar (non-patented in the United States) during 1994 at Dax (Les Landes), France. The male parent (i.e., the pollen parent) is unknown.

The parentage of the new cultivar can be summarized as follows:

'Eichholz'×Unknown.

The resulting seeds were sown at Angers (Maine et Loire), France, and small plantlets were obtained which were physically and biologically different from each other. Selective study resulted in the identification of a single plant of the present invention.

It was found that this new *Cotoneaster dammeri* cultivar exhibits the following combination of characteristics:

(a) forms attractive dense medium green foliage that is semi-glossy on the upper surface and dull and pubescent on the under surface, (b) exhibits a creeping growth habit with erect branching, (c) is well suited use as an attractive low-growing ornamental ground cover, (d) displays very good tolerance to fire blight (*Erwinia amylovora*), and (e) displays good winter hardiness.

The new cultivar well meets the needs of the horticultural industry and can be used to provide attractive green ornamentation in the landscape. It is particularly well suited for use as a dense ground cover.

The very good tolerance to fire blight (*Erwinia amylovora*) is atypical for previously known *Cotoneaster* cultivars. Also, the winter hardiness is good with plants having withstood temperatures of −10° C. and −12° C. when growing in pots as well as in the field at Angers (Maine et Loire), France.

Plants of the new cultivar can be readily distinguished from their ancestors and other previously known *Cotoneaster* cultivars. For instance, the 'Eichholz' cultivar displays substantially less tolerance to fire blight as well as considerably less erect branching. The new cultivar is more vigorous and more erect than the 'Streibsfindling' cultivar (non-patented in the United States), and displays an overall smaller growth habit than the 'Stogholm' cultivar (non-patented in the United States).

The rooting of cuttings has been used to asexually reproduce the new cultivar of the present invention at Angers (Maine et Loire), France. The characteristics of the new cultivar have been shown to be stable and to be firmly fixed following such asexual reproduction. The new cultivar asexually reproduces true to type from one generation to another.

The new cultivar of the present invention has been named 'Belka'.

BRIEF DESCRIPTION OF THE PHOTOGRAPHS

The accompanying photographs illustrate the new cultivar in color as nearly true as it is reasonably possible to make the same in color illustrations of this nature. The plants were grown outside in full sun in containers and in the landscape at Angers (Maine et Loire), France.

FIG. 1—illustrates a typical mature four year-old plant while growing in a container. The erect branching is readily apparent.

Figure 2:
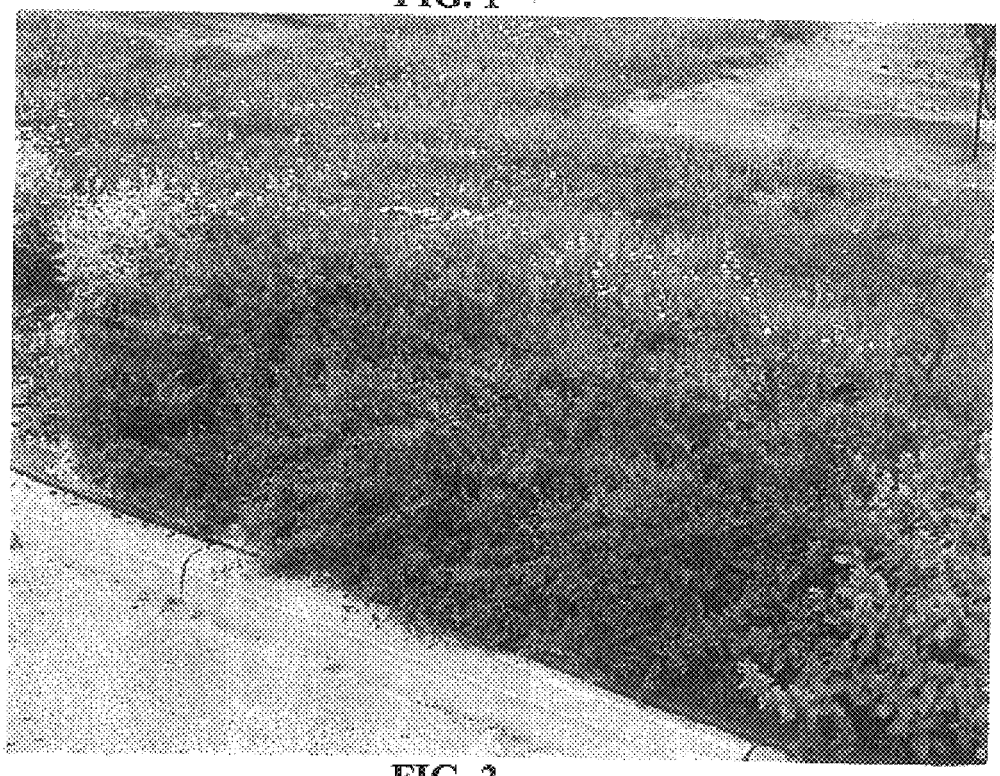

FIG. 2—illustrates typical three year-old plants while growing as a border in the landscape. The dense medium green foliage and creeping growth habit with erect branching are illustrated.

Figure 3:
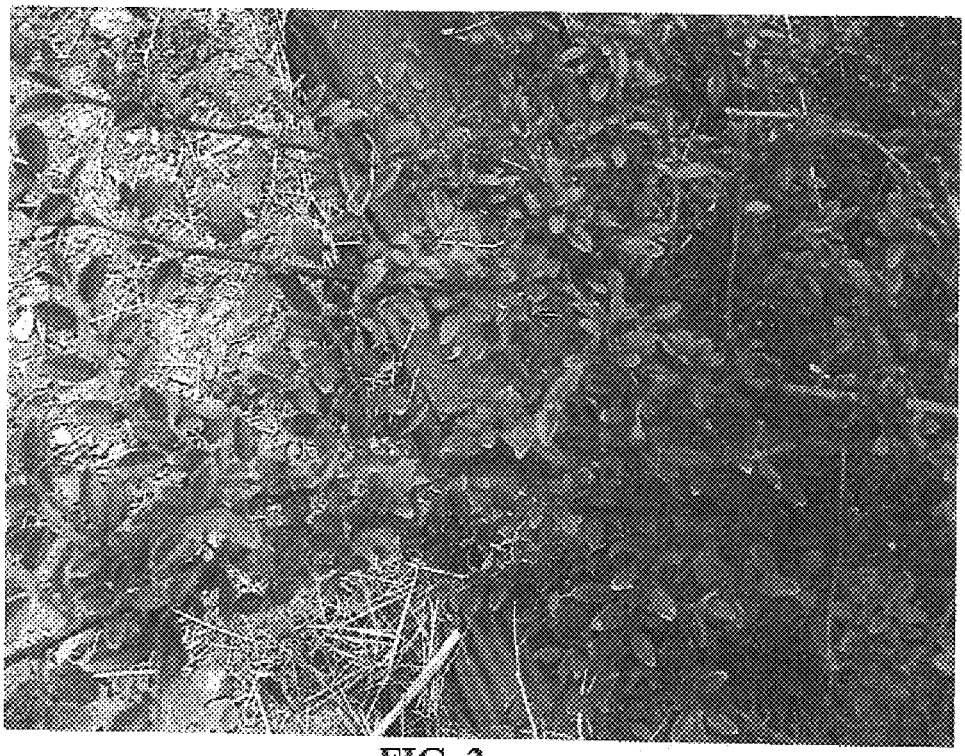

FIG. 3—illustrates typical stems, and foliage together with bright red hips.

Figure 4:
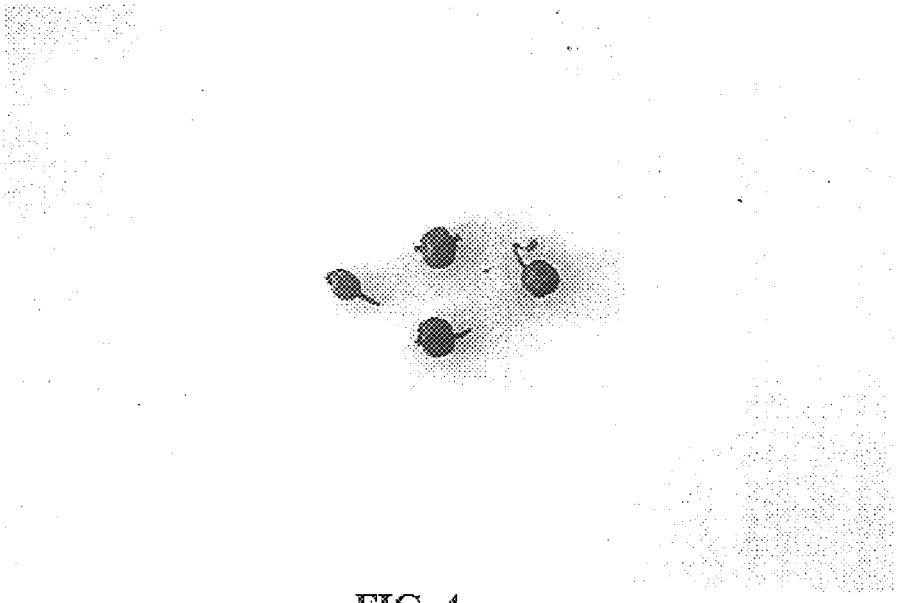

FIG. 4—illustrates four typical bright red hips with tiny adhering peduncles.

Figure 5:
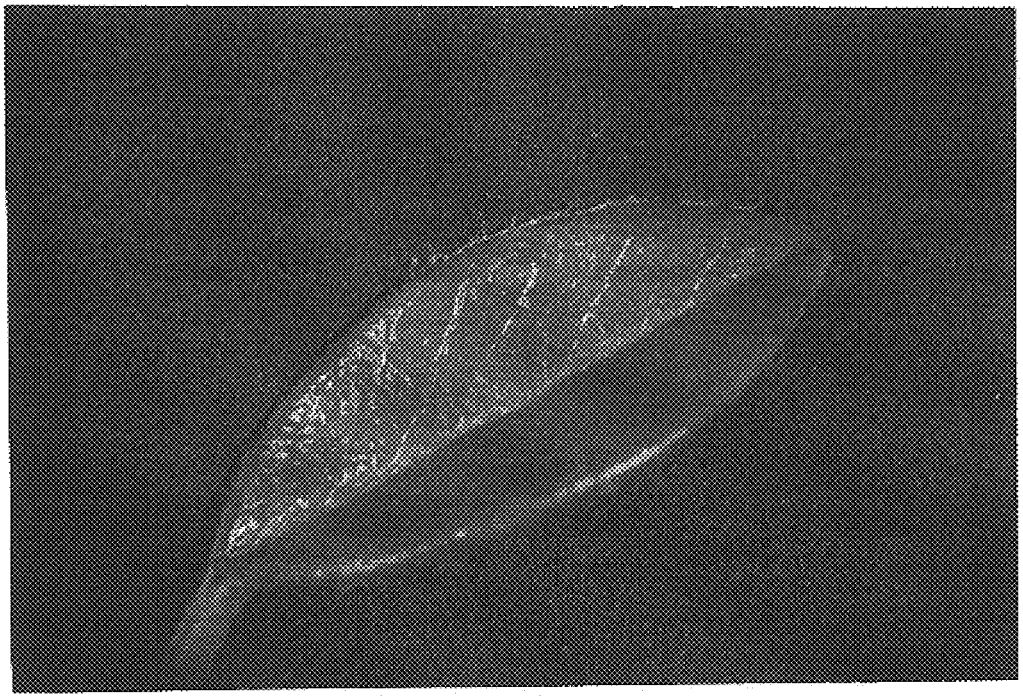

FIG. 5—illustrates the semi-glossy upper surface of a typical mature leaf.

Figure 6:
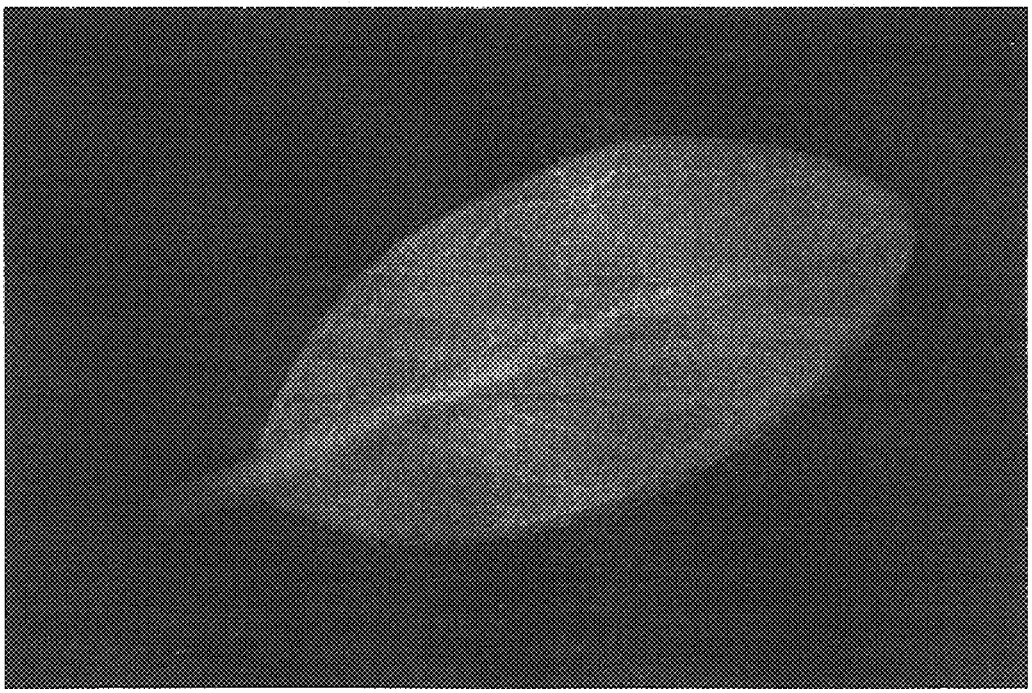

FIG. 6—illustrates the dull pubescent under surface of a typical mature leaf.

Figure 7:
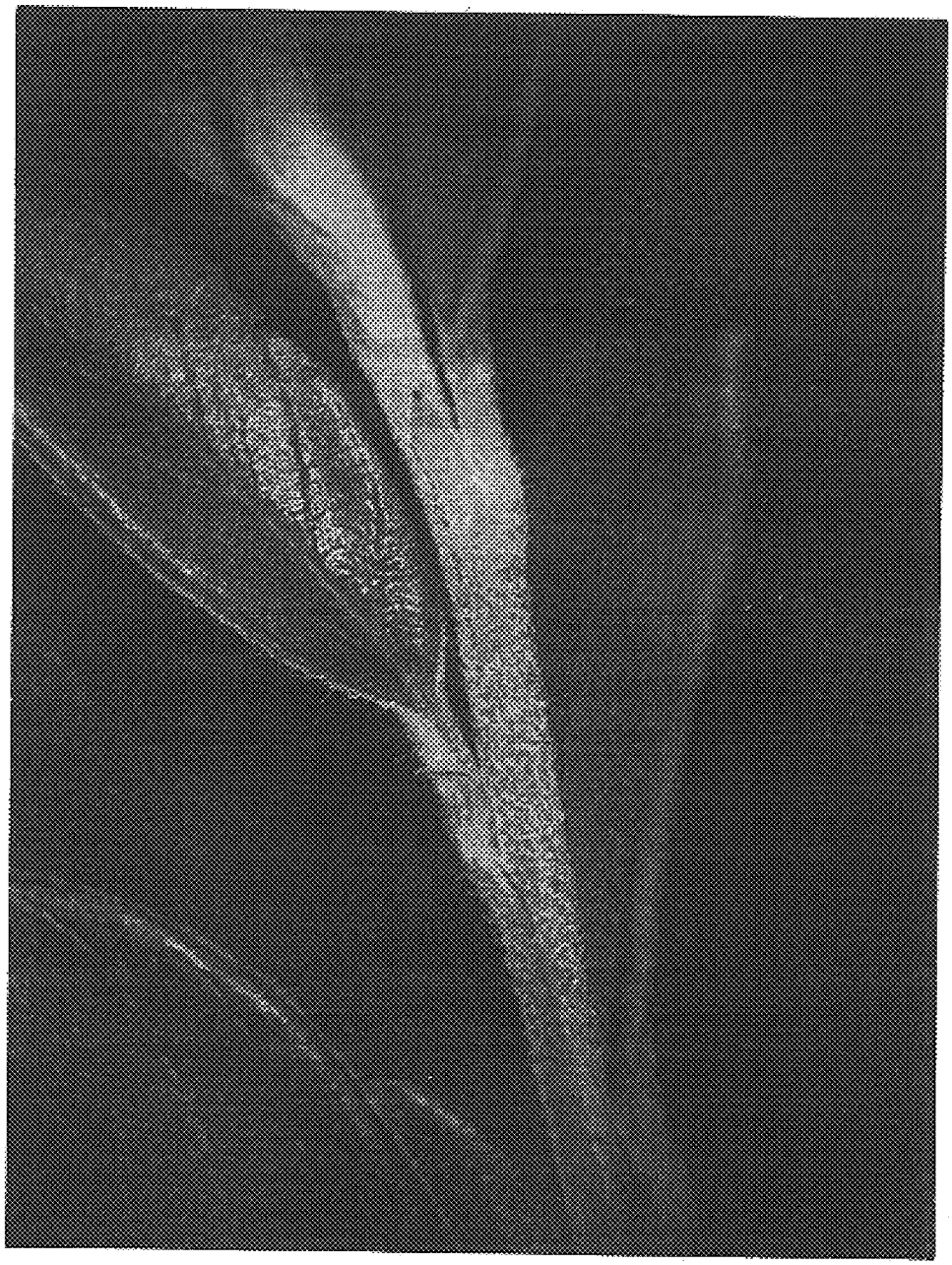

FIG. 7—illustrates a typical young pubescent stem with foliage.

Figure 8:
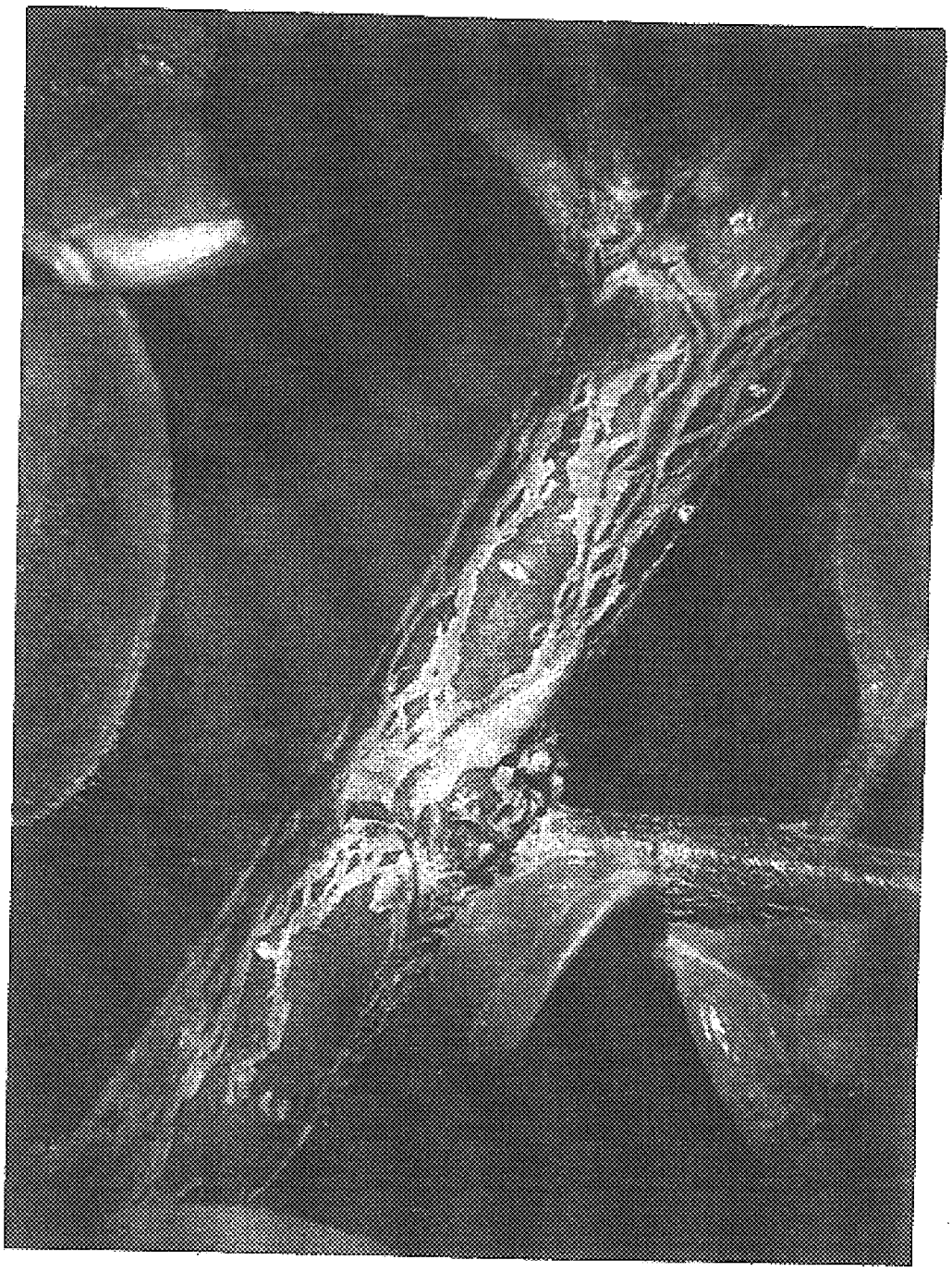

FIG. 8—illustrates a typical mature marbled brown stem with some foliage also being visible.

DETAILED DESCRIPTION

The following is a detailed description while observing mature plants of the new cultivar following the rooting of cuttings. Such plants were approximately four years of age and were observed while growing outdoors in full sun at Angers (Maine et Loire), France. Color terminology is in accordance to The R.H.S. Colour Chart of The Royal Horticultural Society, London.

Plant:

*Growth habit.*—Creeping with erect branching.

*Height.*—Approximately 25 to 35 cm on average.

*Width.*—Approximately 60 to 75 cm on average.

Branches:

*Stem length.*—Approximately 20 to 30 cm on average.

*Young stems.*—Near Greyed-Purple Group 183B with dense pubescence near Yellow-Green Group 145C in coloration.

*Adult stems.*—Near Greyed-Orange Group 177A marbled with Greyed-Green Group 189D in coloration, and smooth and glossy.

Foliage:

*General appearance.*—Rather dense.

*New foliage.*—Upper Surface: Semi-glossy and near Green Group 137C in coloration, and the under surface is near Yellow-Green Group 147D in coloration. Under Surface: Dull, pubescent, and near Yellow-Green Group 147D in coloration.

*Mature foliage.*—Upper Surface: Near Green Group 137A in coloration, and smooth and glossy. Under Surface: Near Yellow-Green Group 148B in coloration, and somewhat pubescent.

*Fall and winter foliage.*—Commonly near Greyed-Red Group 181A to Greyed-Purple Group 184A and 184B in coloration.

*Shape.*—Generally elliptical.

*Bearing.*—Simple (one leaflet).

*Length.*—Approximately 1.76 cm on average.

*Width.*—Approximately 0.9 cm at widest point on average.

*Margin.*—Entire.

*Apex.*—Generally obtuse.

*Base.*—Generally obtuse to cuneate.

*Petiole.*—Approximately 0.4 to 0.5 cm in length on average, rigid, pubescent on the upper and under surfaces, near Greyed-Red Group 178A and 178B on the upper surface, and near Yellow-Green Group 145C on the under surface.

Inflorescence:

*Blooming time.*—Mid-season in May and June.

*Number.*—Commonly in corymbs of 2 or 3 flowers, and sometimes solitary.

*Petal number.*—Five.

*Diameter.*—Approximately 0.5 cm on average.

*Color.*—Near White Group 155A.

*Stamen number.*—Approximately 20 arranged in two rows.

*Stamen color.*—Near Yellow-White Group 158C and 158D for the filaments and anthers.

*Filament length.*—Approximately 1.5 to 2 mm on average.

*Pollen.*—Present, and commonly near Greyed-Purple Group 184A and 184B in coloration.

*Pistil number.*—Three.

*Pistil color.*—Near Yellow-Green Group 145B for the styles and stigmas.

*Style length.*—Approximately 2.5 to 3.5 mm on average.

*Hips.*—Rounded to obovate in configuration, firm, smooth, commonly approximately 0.45 cm in length on average, commonly 0.45 cm in width on average, and near Greyed-Red Group 181A in coloration.

*Seeds.*—Elongated in configuration, smooth, commonly three per hip, and the coloration is near Greyed-Orange Group 164B and 164C with Greyed-Red Group 179B and 179C at the tip.

*Sepals.*—Five in number, approximately 1.5 to 2 mm in length on average, and near Yellow-Green Group 145B and 145C in coloration with tips of near Greyed-Red Group 180A and 180B.

*Peduncles.*—The longer peduncles of corymbs commonly are approximately 6 to 8 mm in length on average, the shorter peduncles of corymbs commonly are approximately 3 to 5 mm in length on average, the diameter commonly is approximately 0.8 mm on average, commonly are covered with fine pubescence, and commonly are near Yellow-Green Group 145B and 145C in coloration.

Disease resistance: Unlike other previously known *Cotoneaster dammeri* cultivars, the new cultivar of the present invention displays very good tolerance to fire blight. (*Erwinia amylovora*). More specifically, it was superior when compared to twenty-two specimens during observation to date. Fire blight commonly has been recognized to be very destructive to *Cotoneaster* plants in the past.

Plants of the new 'Belka' cultivar have not been observed under all possible environmental conditions to date. Accordingly, it is possible that the phenotypic expression may vary somewhat with changes in light intensity and duration, cultural practices, and other environmental conditions.

We claim:

1. A new and distinct *Cotoneaster dammeri* plant having the following combination of characteristics:

(a) forms attractive dense medium green foliage that is semi-glossy on the upper surface and dull and pubescent on the under surface, (b) exhibits a creeping growth habit with erect branching, (c) is well suited for use as an attractive low-growing ornamental ground cover, (d) displays very good tolerance to fire blight (*Erwinia amylovora*), and (e) displays good winter hardiness;

substantially as herein illustrated and described.

* * * * *